United States Patent [19]
Vlasblom

[11] Patent Number: 5,728,662
[45] Date of Patent: Mar. 17, 1998

[54] GEL HAND CLEANER

[75] Inventor: Jack T. Vlasblom, Dunedin, Fla.

[73] Assignee: Dotolo Research Corporation, Largo, Fla.

[21] Appl. No.: 676,067

[22] Filed: Jul. 5, 1996

[51] Int. Cl.$^6$ .............................. A61K 7/50; A61K 7/48; C11D 17/00; A41D 19/00

[52] U.S. Cl. .............. 510/130; 510/131; 510/138; 510/159; 510/403; 510/421; 510/422; 510/463; 252/106; 252/162; 252/171; 252/173; 514/159

[58] Field of Search .................... 252/106, 162, 252/173, 171; 514/159; 510/130, 131, 138, 159, 403, 421, 422, 463

[56] References Cited

U.S. PATENT DOCUMENTS

| | | | |
|---|---|---|---|
| 3,293,179 | 12/1966 | Butcosk | 252/18 |
| 3,933,674 | 1/1976 | Farnsworth | 252/71 |
| 4,374,745 | 2/1983 | Sibley et al. | 252/106 |
| 4,800,196 | 1/1989 | Nomura et al. | 514/159 |
| 5,587,357 | 12/1996 | Rhinesmith | 510/417 |

*Primary Examiner*—Mukund J. Shah
*Assistant Examiner*—Tamthom T. Ngo
*Attorney, Agent, or Firm*—Donald R. Fraser

[57] ABSTRACT

A gel hand cleaner consists essentially of d-limonene, a solvent, C-11 alcohol ethoxylate, polyoxyethylene (20) sorbitan monooleate, a water-soluble acrylic polymer, sodium hydroxide, mixed isothiazolinones, 2,6-di-tert-butyl-p-cresol, and the balance, water.

15 Claims, No Drawings

GEL HAND CLEANER

FIELD OF THE INVENTION

The present invention relates generally to a gel hand cleaner. More particularly, the present invention is directed to a thickened citrus gel waterless hand cleaner containing, inter alia, d-limonene.

BACKGROUND OF THE INVENTION

Hand cleaners generally are made from simple mixtures of sodium salts of long-chain fatty acids. Perfumes, dyes, and germicides many times are added to conventional hand cleaners. Moreover, it is known to add polymeric thickeners to hand cleaners to produce a gel hand cleaner formulation. The polymeric thickeners of the prior art, however, generally are not water-soluble, but rather are water-dispersable and must be pre-emulsified or pre-dispersed in water in order to be useful for making gel hand cleaners. This limits the use of such water-dispersable polymeric thickeners since they are difficult to incorporate into hand cleaners by a continuous production process without the materials prematurely undergoing polymerization in the passageways of the process equipment. This solids build-up results in premature process equipment failure.

It would be desirable to formulate a thickened citrus gel waterless hand cleaner utilizing a water-soluble polymeric thickener.

SUMMARY OF THE INVENTION

Accordant with the present invention, a thickened citrus gel waterless hand-cleaner surprisingly has been discovered. The hand cleaner consists essentially of d-limonene, a solvent, C-11 alcohol ethoxylate, polyoxyethylene (20) sorbitan monooleate, a water-soluble acrylic polymer, sodium hydroxide, mixed isothiazolinones, 2,6-di-tert-butyl-p-cresol, and the balance, water. The inventive formulation is particularly useful for cleaning one's hands.

DETAILED DESCRIPTION OF THE PREFERRED EMBODIMENT

The gel hand cleaner according to the present invention consists essentially of a combination of d-limonene, a solvent, C-11 alcohol ethoxylate, polyoxyethylene (20) sorbitan monooleate, a water-soluble acrylic polymer, sodium hydroxide, mixed isothiazolinones, 2,6-di-tert-butyl-p-cresole, and the balance, water.

D-limonene is a terpene which occurs naturally in all living plants. It is a monocyclic unsaturated terpene which generally is a byproduct of the citrus industry, derived from the distilled rind oils of oranges, grapefruits, lemons, and the like. A discussion regarding d-limonene and its derivation from numerous sources is set forth in Kesterson, J. W. "Florida Citrus Oil," Institute of Food and Agriculture Sciences, University of Florida, December, 1971. D-limonene is commercially available from Florida Chemical Company and from SMC Glidco Organics. D-limonene may be present in the inventive formulation at a concentration from about 2 to about 60 weight percent. Preferably, the concentration ranges from about 3 to about 10 weight percent.

The inventive gel hand cleaner according to the present invention includes a solvent which assists the d-limonene in dissolving grease and oil. The solvent may comprise a terpene such as that available from Environmental Solvents Corporation under the product designation "REENTRY", an olefin such as that available from Shell Chemicals under the product designation "NEOSOLV 2" or that available from Textile Scientific Polymers, Inc. under the product designation "TEXPOL 200D", a dibasic acid ester such as, for example, dimethyl adipate, dimethyl glutarate, or dimethyl succinate, naphthenic solvents such as those available from Exxon under the product designations "EXXSOL D-60", "EXXSOL D-80", or "EXXSOL D-100", a polar solvent such as N-methyl-2-pyrrolidone or propylene carbonate, glycol ethers such as those available from Dow Chemical under the product designations "DOWANOL DPNB" and "PROGLYDE", and the like, as well as mixtures thereof. A preferred solvent is a terpene. The solvent may be present at a concentration ranging from about 2 to about 60 weight percent. Preferably, the concentration ranges from about 3 to about 10 weight percent.

C-11 alcohol ethoxylate is present as a detergent in the gel hand cleaner according to the present invention. The concentration of the C-11 alcohol ethyoxylate may range from about 0.5 to about 50 weight percent. Preferably, the concentration ranges from about 2.5 to about 10 weight percent. A preferred C-11 alcohol ethoxylate is available from Van Waters and Rogers, Inc. under the product designation "NEODOL 1-5".

Polyoxyethylene (20) sorbitan monooleate is present in the inventive formulation as a stabilizer. A preferred polyoxyethylene (20) sorbitan monooleate may be obtained from Van Waters and Rogers, Inc. under the product designation "TWEEN 80". The concentration of the polyoxyethylene (20) sorbitan monooleate may range from about 0.25 to about 20 weight percent. Preferably, the concentration ranges from about 0.5 to about 5 weight percent.

The hand cleaner formulation according to the present invention utilizes a water-soluble acrylic polymer emulsifier. A preferred water-soluble acrylic polymer may be obtained from B. F. Goodrich Specialty Chemicals under the product designation "CARBOPOL ULTREZ 10". The water-soluble acrylic polymer emulsifier may be present at a concentration from about 0.25 to about 20 weight percent. Preferably, the concentration ranges from about 0.5 to about 5 weight percent.

The inventive gel hand cleaner according to the present invention includes sodium hydroxide, a well-known commercially available compound. The sodium hydroxide may be present at a concentration ranging from about 0.1 to about 5 weight percent. Preferably, the concentration ranges from about 0.1 to about 1 weight percent.

Mixed isothiazolinones are present in the inventive gel hand cleaner according to the present invention as a biocide. Useful isothiazolinones include, but are not necessarily limited to, 5-chloro-2-methyl-4-isothiazolin-3-one, 2-methyl-4-isothiazolin-3-one, and mixtures thereof. A preferred isothiazolinone mixture may be obtained from Rohm and Haas Company under the product designation "KATHON CG". The isothiazolinone may be present at a concentration ranging from about 0.001 to about 0.1 weight percent. Preferably, the concentration ranges from about 0.001 to about 0.01 weight percent.

The invention gel hand cleaner additionally contains 2,6-di-tert-butyl-p-cresol as an antioxidant. The 2,6-di-tert-butyl-p-cresol is present at a concentration from about 0.02 to about 4 weight percent. Preferably, the concentration ranges from about 0.1 to about 0.5 weight percent. A preferred 2,6-di-tert-butyl-p-cresol may be obtained from Uniroyal Chemical Company, Ind. under the product designation "NAUGARD BHT".

Water is present in the inventive gel hand cleaner as a matrix for the emulsified organic phase. The concentration of water may vary over wide limits from about 25 to about 95 weight percent and comprises the balance of the formulation by weight. Preferably, the concentration of water ranges from about 75 to about 85 weight percent.

The use of the water-soluble acrylic polymer in the gel hand cleaner according to the present invention, and the attendant ability to manufacture said gel hand cleaner utilizing continuous process equipment without plugging the passageways thereof, yields considerable advantages over the formulations and manufacturing processes of the prior art which relay on conventional surfactant/soap technology to achieve a gel product. It is observed that the strong base neutralized flowable gel product according to the present invention is stable upon exposure to the atmosphere over several days, as opposed to only several hours for conventional gel hand cleaners.

Moreover, the gel hand cleaner formulation according to the present invention results in considerable flexibility regarding the kinds of solvents which may be used. This is because the present formulation does not rely upon the surfactant/soap base to produce a thickened hand cleaner. Such flexibility allows for the adjustment of the solvent component of the inventive gel hand cleaner formulation to suit market conditions such as desired product characteristics and solvent availability.

EXAMPLE

The following ingredients are mixed together utilizing a conventional continuous process mixer, e.g., a Bran & Luebbe metering system, in the approximate weight percentages indicated.

TABLE I

GEL HAND CLEANER FORMULATION

| INGREDIENT | WEIGHT PERCENT |
| --- | --- |
| d-limonene (1) | 5 |
| solvent (2) | 5 |
| C-11 alcohol ethoxylate (3) | 4 |
| polyoxyethylene (20) sorbitan monooleate (4) | 1 |
| water-soluble acrylic polymer (5) | 1.2 |
| sodium hydroxide | 0.4 |
| isothiazolone (6) | 0.002 |
| 2,6-di-tert-butyl-p-cresol (7) | 0.15 |
| water | 83.248 |

(1) GLIDSAFE; SMC Glidco Organics
(2) REENTRY; REENTRY ® Environmental Solvents Co.
(3) NEODOL 1-5; Van Waters and Rogers, NEODOL ® Shell Chemical Co.
(4) TWEEN 80; Van Waters and Rogers, TWEEN ® ICI Chemicals Co. - U.K.
(5) CARBOPOL ULTREZ 10; B. F. Goodrich Specialty Chemicals
(6) KATHON CG; Rohm and Haas Company
(7) NAUGARD BHT; Uniroyal Chemical Company The resultant gel hand cleaner has an opaque white color and may be characterized as "flowable" gel. It has an approximate average viscosity of about 75,000 centipoise at 25° C. The gel hand cleaner has a pH of from about 5.5 to about 6.5, and a pleasant citrus odor. The gel hand cleaner effectively removes dirt, grease, and oil from one's hands, yet is mild to the skin.

This Example may be repeated with similar success by substituting the generically or specifically described ingredients and/or concentrations recited herein for those used in the preceding Example.

From the foregoing description, one ordinarily skilled in the art can easily ascertain the essential characteristics of this invention, and without departing from its spirit and scope, can make various changes and modifications to the invention to adapt it to various usages and conditions.

What is claimed is:

1. A gel hand cleaner, consisting essentially of:

from about 2 to about 60 weight percent d-limonene;

from about 2 to about 60 weight percent solvent;

from about 0.5 to about 50 weight percent C-11 alcohol ethoxylate;

from about 0.25 to about 20 weight percent polyoxyethylene (20) sorbitan monooleate;

from about 0.25 to about 20 weight percent water-soluble acrylic polymer;

from about 0.1 to about 5 weight percent sodium hydroxide;

from about 0.001 to about 0.1 weight percent mixed isothiazolinones;

from about 0.02 to about 4 weight percent 2,6-di-tert-butyl-p-cresol; and the balance water.

2. The gel hand cleaner according to claim 1, wherein the solvent is selected from the group consisting of a terpene, an olefin, a dibasic acid ester, a naphthenic solvent, a polar solvent, and mixtures thereof.

3. The gel hand cleaner according to claim 1, wherein the isothiazolone is a mixture of 5-chloro-2-methyl-4-iosothiazolin-3-one and 2-methyl-4-isothiazolin-3-one.

4. The gel hand cleaner according to claim 1, wherein the concentration of d-limonene ranges from about 3 to about 10 weight percent.

5. The gel hand cleaner according to claim 1, wherein the solvent concentration ranges from about 3 to about 10 weight percent.

6. The gel hand cleaner according to claim 1, wherein the concentration of C-11 alcohol ethoxylate ranges from about 2.5 to about 10 weight percent.

7. The gel hand cleaner according to claim 1, wherein the concentration of polyoxyethylene (20) sorbitan monooleate ranges from about 0.5 to about 5 weight percent.

8. The gel hand cleaner according to claim 1, wherein the water-soluble acrylic polymer concentration ranges from about 0.5 to about 5 weight percent.

9. The gel hand cleaner according to claim 1, wherein the concentration of sodium hydroxide ranges from about 0.1 to about 1 weight percent.

10. The gel hand cleaner according to claim 1, wherein the mixed isothiazolinones concentration ranges from about 0.001 to about 0.01 weight percent.

11. The gel hand cleaner according to claim 1, wherein the concentration of 2,6-di-tert-butyl-p-cresol ranges from about 0.1 to about 0.5 weight percent.

12. A gel hand cleaner, consisting essentially of:

from about 3 to about 10 weight percent d-limonene;

from about 3 to about 10 weight percent solvent;

from about 2.5 to about 10 weight percent C-11 alcohol ethoxylate;

from about 0.5 to about 5 weight percent polyoxyethylene (20) sorbitan monooleate;

from about 0.5 to about 5 weight percent water-soluble acrylic polymer;

from about 0.1 to about 1 weight percent sodium hydroxide;

from about 0.001 to about 0.01 weight percent mixed isothiazolinones;

from about 0.1 to about 0.5 weight percent 2,6-di-tert-butyl-p-cresol; and the balance, water.

13. The gel hand cleaner according to claim 12, wherein the solvent is selected from the group consisting of a terpene, an olefin, a dibasic acid ester, a naphthenic solvent, a polar solvent, and mixtures thereof.

14. The gel hand cleaner according to claim 12, wherein the isothiazolone is a mixture of 5-chloro-2-methyl-4-isothiazolin-3-one and 2-methyl-4-isothiazolin-3-one.

15. A gel hand cleaner, consisting essentially of:

from about 3 to about 10 weight percent d-limonene;

from about 3 to about 10 weight percent solvent comprising a solvent selected from the group consisting of a terpene, an olefin, a dibasic acid ester, a naphthenic solvent, a polar solvent, and mixtures thereof;

from about 2.5 to about 10 weight percent C-11 alcohol ethoxylate;

from about 0.5 to about 5 weight percent polyoxyethylene (20) sorbitan monooleate;

from about 0.5 to about 5 weight percent water-soluble acrylic polymer;

from about 0.1 to about 1 weight percent sodium hydroxide;

from about 0.001 to about 0.01 weight percent of a mixture comprising 5-chloro-2-methyl-4-isothiazolin-3-one and 2-methyl-4-isothiazolin-3-one;

from about 0.1 to about 0.5 weight percent 2,6-di-tert-butyl-p-cresol; and the balance, water.

* * * * *